United States Patent [19]

Ward

[11] 4,008,290

[45] Feb. 15, 1977

[54] CUMENE PRODUCTION

[75] Inventor: Dennis J. Ward, South Barrington, Ill.

[73] Assignee: UOP Inc., Des Plaines, Ill.

[22] Filed: Apr. 19, 1976

[21] Appl. No.: 678,005

Related U.S. Application Data

[63] Continuation-in-part of Ser. No. 557,010, March 10, 1975, abandoned.

[52] U.S. Cl. .......................... 260/672 T; 260/671 P
[51] Int. Cl.² .......................... C07C 3/62; C07C 3/54
[58] Field of Search ........ 260/671 P, 672 T, 671 R, 260/671 C

[56] References Cited

UNITED STATES PATENTS

| | | | |
|---|---|---|---|
| 2,860,173 | 11/1958 | Jones et al. | 260/671 P |
| 2,864,874 | 12/1958 | Enos | 260/671 P |
| 3,183,233 | 5/1965 | Bloch | 260/671 R |
| 3,527,823 | 9/1970 | Jones | 260/671 P |

OTHER PUBLICATIONS

Chem. Abs., 74 125855.

*Primary Examiner*—C. Davis
*Attorney, Agent, or Firm*—James R. Hoatson, Jr.; Robert W. Welch; William H. Page, II

[57] ABSTRACT

A process to reduce utility consumption in the catalytic alkylation of benzene with propylene to form cumene. Propylene and benzene are reacted in an alkylation reaction zone, the effluent of which is divided into two portions, the first being recirculated to the inlet of the reaction zone and the second being passed into a separation zone wherein cumene product, di- and triisopropylbenzene and excess benzene are separated. A portion of the excess benzene is recycled to the inlet of the alkylation reaction zone, and a second portion is admixed with di- and triisopropylbenzene and passed into a transalkylation zone, the effluent of which is introduced into the separation zone. Utility consumption is reduced compared to prior art processes, as a result of a reduction of the portion of excess benzene separated and recycled to the alkylation reaction zone.

11 Claims, 1 Drawing Figure

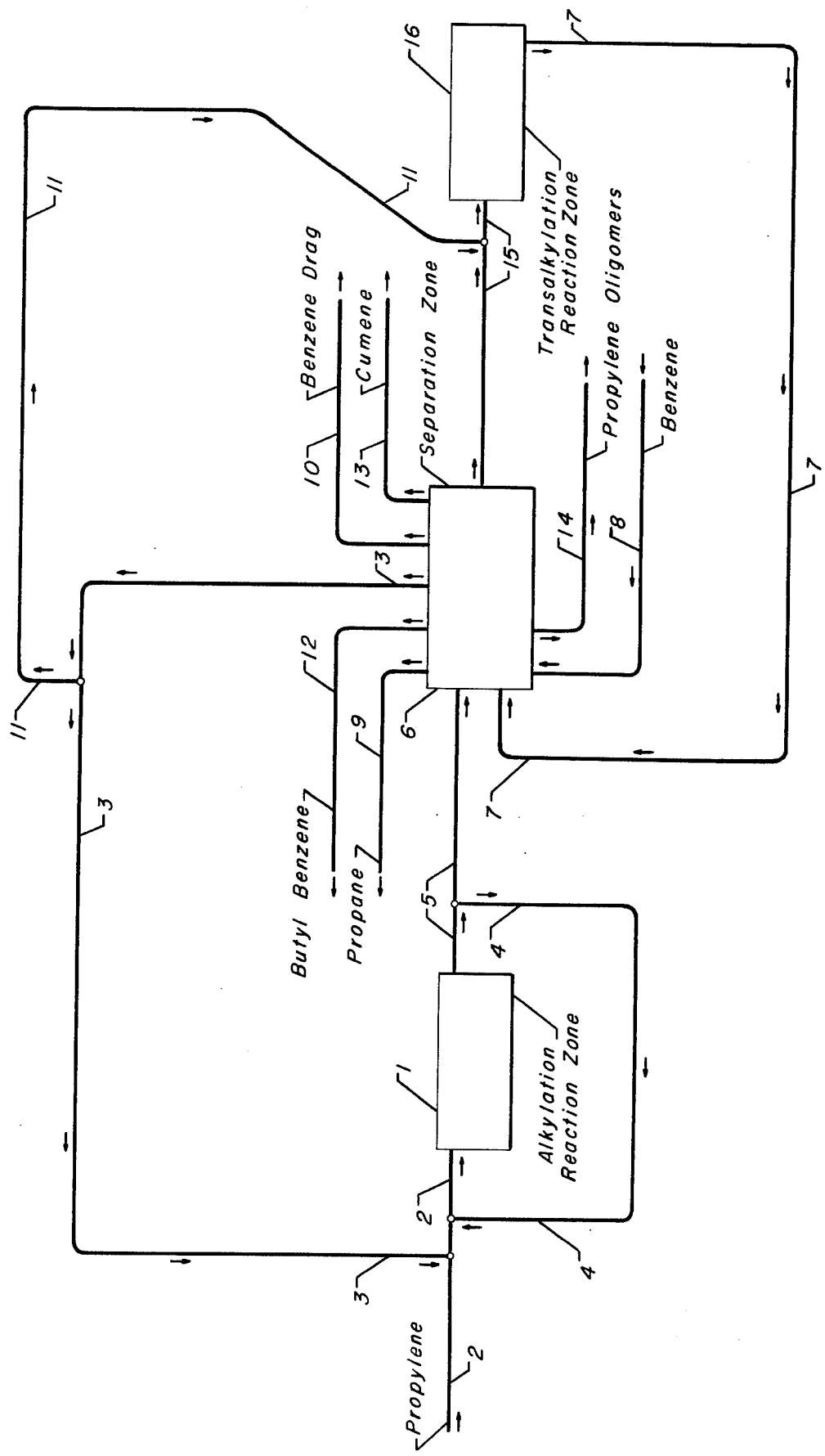

1

CUMENE PRODUCTION

CROSS-REFERENCE TO RELATED APPLICATIONS

This application is a continuation-in-part application of a copending application Ser. No. 557,010, filed Mar. 10, 1975, and now abandoned.

BACKGROUND OF THE INVENTION

This invention relates to an improved process for producing cumene from benzene and propylene in the presence of an alkylation catalyst. It also relates to transalkylating di- and triisopropylbenzene with benzene in the presence of a transalkylation catalyst to produce cumene.

The present invention is broadly applicable to the production of alkylated aromatic hydrocarbons. These compounds are useful in themselves and more frequently in subsequent chemical synthesis of other compounds. The present invention is particularly applicable to the production of cumene, or isopropylbenzene, which is a reactant finding utility in the preparation of phenol, acetone, alphamethylstyrene and acetophenone. Another application of the process of the present invention may be found in the preparation of p-cymene which may be oxidized to produce p-cresol. A further application of the process is in the alkylation of a substituted aromatic compound such as phenol, which when alkylated with isobutylene forms o-tertiary-butylphenol and p-tertiary-butylphenol, both of which find utility in the resin field.

As above stated, the present invention finds particular application in the preparation of cumene. In the usual commercial process for the production of cumene, it is the practice to charge liquid benzene and liquid propylene into a reactor and to react the same therein in one or more alkylation zones in contact with an alkylation catalyst. In order to minimize the production of dialkylated products of benzene it has been the practice to maintain a molar excess of benzene throughout the reaction zone ranging from about 4:1 to about 16:1, and more preferably about 8:1 of benzene to propylene. Two competing reactions with the desired production of isopropylbenzene have created problems in the prior commercial processes used. One of these as indicated above has been the formation of dialkylated benzenes such as di- and triisopropylbenzene rather than the desired monoalkylated product. This competing reaction has been controlled by means of employing large molar excesses of benzene as indicated above. The other competing reaction causing losses in the yield of cumene based on propylene reactant charged is the formation of oligomers of propylene such as propylene dimer and trimer which occur to a limited extent even with the large molar excesses of benzene present. Propylene trimers and some of the propylene tetramers boil with cumene. Since the presence of these olefins interfere with the oxidation reaction used to make phenol from cumene, this oligomerization side reaction must be minimized to make a high purity product.

The alkylation reaction of the alkylatable aromatic compound is exothermic in nature and the temperature within the reactor tends to increase at a rapid rate. This increase in temperature caused by the exothermic reaction likewise tends to increase the production of cumeme bottoms products by the competing reactions.

In the past it has been customary to control the temperature rise by catalyzing the reaction in multiple separate zones and employing a quenching medium between each of several successive alkylation zones. This quenching has served to control the temperature at which the reaction mixture enters each successive zone and thus the temperature rise throughout each zone. The temperature rise from inlet to outlet of the reactor has also been controlled by controlling the molar excess of benzene charged to the reactor, the benzene acting as a heat sink to absorb heat released by the alkylation reaction. Accordingly, increasing the molar excess of benzene charged to the reactor, with a corresponding dilution of the propylene reactant therein, not only provides more aromatic sites subject to alkylation and a resulting reduction in oligomers and over alkylated by-products, but also reduces the formation of undesirable by-products resulting from an excessive temperature rise across an alkylation zone or zones.

To obtain the desired high molar excess of benzene in the reactor charge, it has been the practice to separate the reaction zone effluent to obtain a benzene-rich stream suitable to recycle to the reactor. Since the two principal components of the reaction zone effluent are benzene and cumene, it is necessary to make a separation of the benzene and cumene, the latter being the higher boiling component. Consequently, to obtain a purified stream of benzene relatively free of cumene and suitable for recycling to the reaction zone, benzene is vaporized and fractionated, thus requiring consumption of substantial heat to vaporize benzene and provide adequate reflux in a benzene fractionator, the heat requirement being substantially proportional to the ratio of benzene to propylene desired in the charge to the reactor. At the present time, relatively high fuel cost necessitates review of processes requiring high utility consumption with the result that alternative processing schemes which previously were unattractive are becoming more desirable if utility consumption is reduced.

SUMMARY OF THE INVENTION

An object of the present invention is to provide an improved process for the alkylation of benzene with propylene to produce cumene in the presence of an alkylation catalyst. A specific object of this invention is to reduce utility consumption in a process for the alkylation of benzene with propylene to produce cumene in the presence of an alkylation catalyst. A more specific object of this invention is to provide a process for the alkylation of benzene with propylene to produce cumene in the presence of a solid phosphoric acid catalyst, the process requiring a relatively lower molar excess of benzene to propylene than prior art processes as provided by recycle of excess benzene separated from the reaction zone effluent.

One embodiment of the present invention relates to a process for the production of cumene which comprises: (a) reacting propylene with an excess of benzene in the presence of an alkylation catalyst at alkylation reaction conditions in an alkylation reaction zone; (b) dividing the total liquid effluent of said zone into at least two portions of like composition; (c) recirculating one of said portions of the effluent to said reaction zone; (d) introducing another of said portions of said effluent and a transalkylation zone effluent stream, formed as hereinafter set forth, into a separation zone; (e) separting from the admixed effluents in the separation zone a benzene-rich stream, a cumene product stream and a di- and triisopropylbenzene-rich stream; (f) transalkylating the last named stream with benzene in the presence of a transalkylation catalyst in a transalkylation zone to form additional cumene; (g) supplying the effluent of the last mentioned zone to said separation zone as said transalkylation zone effluent stream; (h) passing at least a portion of said benzene-rich stream from the separation zone to said alkylation reaction zone; and (i) recovering said cumene product stream from the separation zone.

In the processing scheme of the present invention, propylene and excess benzene are reacted in an alkylation reaction zone wherein an alkylation catalyst is employed, and a portion of the resultant effluent is recirculated without separation to the inlet of the reaction zone. A second portion of reaction zone effluent, i.e., net effluent, is passed into a separation zone in which excess benzene, cumene, di- and triisopropylbenzene, and other components are separated. As stated hereinabove, it is desirable to reduce the quantity of excess benzene separated from the net effluent stream in order to reduce utility consumption, while at the same time it is desired to maintain a sufficient quantity of excess benzene in the reaction zone to prevent excessive formation of propylene oligomers. This is accomplished by recirculation of a portion of the resultant reaction zone effluent without separation. The principal effects of process operation in the hereinabove described manner include: (1) a reduction of utility consumption resulting from a reduction of excess benzene separated from cumene in the net reaction zone effluent stream; and (2) formation of relatively more di- and trialkylated benzene products than in processes known in the prior art. In the separation zone of the present process, di- and triisopropylbenzenes are concentrated and passed in admixture with excess benzene into a transalkylation reaction zone, wherein a transalkylation catalyst is employed in a preferred embodiment. The cumene-rich transalkylation reaction zone effluent stream is returned to the separation zone.

DESCRIPTION OF THE DRAWING

This invention can be more clearly described and illustrated with reference to the attached drawing. While of necessity, certain limitations must be present in such a schematic description, no intention is meant thereby to limit the generally broad scope of the invention. As stated hereinabove, the first step of the process of the present invention comprises alkylating benzene with propylene in an alkylation reaction zone in the presence of an alkylation catalyst. In the drawing, this first step is represented as taking place in alkylation reaction zone 1. However, a mixture of benzene and propylene must be furnished to this reaction zone. In the drawing, a propylene-rich feed stream is supplied to the alkylation zone 1 via conduit 2; benzene is prepared as a recycle stream as hereinbelow described and furnished to the alkylation zone 1 via conduit 3, which combines with conduit 2; and an alkylation zone effluent recirculation stream including principally benzene and cumene is prepared as described hereinbelow and furnished to the alkylation zone inlet via conduits 4 and 2. The lastly mentioned stream provides additional benzene for the purpose of increasing the molar benzene/propylene ratio in the alkylation reaction zone. The combined mixture of propylene reactant, recycle benzene, and recirculated reaction zone effluent is then introduced into reaction zone 1 via conduit 2. Effluent of the alkylation reaction zone 1 is withdrawn via conduit 5, a portion is recirculated via conduit 4 to provide the recirculation stream described hereinabove, and the remaining portion is passed via conduit 5 into a separation zone 6. Also introduced into the separation zone 6 is an effluent stream from a transalkylation reaction zone as described hereinbelow, the transalkylation zone effluent stream passing through conduit 7. A benzene feed stream via conduit 8 is also introduced into the separation zone 6 of the present process.

The propylene-rich feed stream supplied to the alkylation reaction zone via conduit 2 can be prepared as an effluent stream from various processes such as fluid catalytic cracking or pyrolysis, and will normally include non-reactive paraffins, principally propane, but also substantially smaller quantities of ethane and butane. Olefins other than propylene result in undesirable products in the alkylation reaction to produce cumene, therefore propylene normally comprises at least 99 percent of the olefin content of this stream. The benzene feed stream introduced into the process in conduit 8 is a high purity stream commonly containing at least 99.5 percent benzene which is frequently available as an effluent stream from an aromatics extraction process. Other aromatics are harmful in the sense that undesirable by-products result from their presence, and non-aromatics are normally undesirable because of difficulty in separation of these non-aromatics from benzene in the separation zone 6. Accordingly, in the present process, the streams introduced into the separation zone 6 include principally benzene, cumene, propane, and di- and triisopropylbenzene, with relatively smaller amounts of light paraffins (ethane and butane), aromatics (toluene and xylene), butylbenzene, and oligomers of propylene.

In the separation zone 6, by suitable combination of flashing, fractionation, absorption, and stripping, several streams are separated to withdraw the inlet components stated hereinabove. A propane-rich product stream including other light praffins is withdrawn via conduit 9; a benzene-rich product drag stream including non-aromatic components is withdrawn via conduit 10; an excess benzene-rich stream is withdrawn via conduit 3, a portion is recycled to the alkylation reaction zone 1 via conduit 3 as hereinabove described and a second portion is passed via conduit 11 to a transalkylation reaction zone as described hereinbelow; a butylbenzene-rich product stream is withdrawn via conduit 12; a cumene product stream is withdrawn via conduit 13; a propylene oligomer product stream is withdrawn via conduit 14; and a di- and triisopropylbenzene-rich stream is withdrawn via conduit 15.

The di- and triisopropylbenzene-rich stream withdrawn from the separation zone via conduit 15 is admixed with recycle benzene via conduit 11, and the mixture is passed into a transalkylation reaction zone 16, which in a preferred embodiment contains a solid phosphoric acid catalyst. Cumene-rich effluent of the transalkylation reaction zone is passed via conduit 7 into the separation zone 6, as described hereinabove.

DETAILED DESCRIPTION OF THE INVENTION

Suitable reactants in the present inventive process to produce cumene are propylene and benzene. Propylene is normally supplied in admixture with propane in an effluent stream from a fluid catalytic cracking unit, a pyrolysis unit, a thermal cracking unit, or other refining unit. Other light paraffinic hydrocarbons such as ethane and butane may be present in limited quantity in a propylene-rich feed stream to the present process, but olefinic compounds other than propylene lead to production of alkylaromatics other than cumene and accordingly are undesirable as a feedstock. A typical propylene feed stream is illustrated as follows in mole percent: ethane 0.10, propane 24.80,propylene 74.95, isobutane 0.11, n-butane 0.01, and butylene 0.03. Benzene is supplied to the present process in high purity, greater than 99.5 percent, to prevent undesirable side reactions and to eliminate additional fractionation requirements to separate benzene and close boiling non-aromatic components within the present process. A typical benzene feed stream is prepared in an aromatics extraction unit and contains the following components in mole percent: benzene 99.90, toluene 0.05, and non-aromatics 0.05. While in the accompanying sketch the benzene feed stream is introduced into the separation zone of the present process, this stream may also be introduced into the alkylation reaction zone or the transalkylation reaction zone.

The inlet stream to the alkylation reaction zone of the present process comprises three streams in admixture; the fresh propylene-rich feed stream, a recirculated portion of the resultant effluent from the alkylation reaction zone as described hereinbelow, and a benzene-rich stream which may be supplied to the present process as a fresh feed stream, or more preferably, as a recycle benzene-rich stream as described hereinbelow. Operating conditions in the alkylation reaction zone include an inlet temperature of about 150° to 260° C. with a preferred temperature of about 195° to 215° C.; about 20 to 60 atmospheres pressure; about 0.2 to 2.0 volumes of catalyst per volume/hour of net reaction zone effluent hereinbelow defined, about 2 to 6 moles of benzene in the recycle benzene-rich stream per mole of propylene in the inlet stream to the alkylation reaction zone, with a preferred molar ratio of recycle benzene to propylene in the inlet stream of about 3; and about 1 to 100 moles of benzene in the recirculated effluent stream per mole of propylene in the inlet stream to the alkylation reaction zone, with a preferred molar ratio of recirculated benzene to propylene in the inlet stream 3 to 20. The process of the present invention may comprise a single reactor or multiple reactors in series or parallel flow, flow through each reactor being downflow, upflow, radial flow, or other, there being no limitation to the inventive concept of the present process by the configuration of reaction zone design.

The process of the present invention can be effected utilizing any conventional or otherwise available alkylation catalyst. Such catalysts are typically described as acid-acting catalysts and may be of the homogeneous or heterogeneous variety. Thus, the catalyst can be a supported or unsupported Friedel Crafts metal halide, for example anhydrous aluminum chloride, ferric chloride, stannic chloride, boron fluoride, zinc chloride and the like. Certain mineral acids, especially sulfuric acid, hydrofluoric acid, and phosphoric acid are known for their capacity to catalyze the alkylation reaction. Sulfuric acid containing less than about 10 wt. % water, hydrofluoric acid of at least 83% concentration, or liquefied anhydrous hydrogen fluoride, are suitably employed. Acid-acting inorganic oxides including phosphorous pentoxide, amorphous silica-alumina, and certain crystalline aluminosilicates or zeolites, particularly acid-extracted mordenite and the Type Y zeolite, are useful as catalysts in the process of this invention.

The present invention is particularly directed to an alkylation reaction in the presence of a solid phosphoric acid catalyst. Thus solid phosphoric acid catalyst which may be utilized in the method of the present invention may be made by mixing an acid of phosphorous, such as ortho-, pyro-, or tetraphosphoric acid and a finely divided, generally siliceous, solid carrier (such as diatomaceous earth, prepared forms of silica, reactivated clays, and the like) to form a wet paste. The paste is then calcined at temperatures generally below about 500° C. to produce a solid cake which is threafter ground and sized to produce particles of useable mesh. If the calcination is carried out at temperatures above about 400° C., it may be desirable to rehydrate the catalyst granules at a temperature between about 200° C. and 350° C., typically 260° C., to produce an acid composition corresponding to high alkylating activity. The catalyst preparation procedure may be varied by forming particles of the original paste by extrusion or by pelleting methods after which the formed particles are calcined and, if necessary, rehydrated. A solid phosphoric acid catalyst prepared from a major proportion by weight of a phosphoric acid having at least as large a water content as that of the pyro acid and a minor proportion of the siliceous carrier, such as kieselguhr, is preferred for use in the present process. In a preferred embodiment of the present invention, the alkylation catalyst includes about 50 to 75 percent by weight phosphoric acid. A further description of a satisfactory solid phosphoric acid catalyst is available in U.S. Pat. No. 1,933,513.

The resultant effluent of the alkylation reaction zone is divided into two streams, the first being a recirculated effluent stream and the second being a net reaction zone effluent stream. An important part of the inventive concept of the present process concerns recirculating a portion of the alkylation reaction zone effluent to the inlet of the alkylation zone to admix with the fresh propylene-rich feed stream and the recycle benzene-rich stream to form the inlet stream to the alkylation reaction zone as described hereinabove. Composition of the alkylation zone effluent is principally benzene with relatively lesser amounts of propane, cumene, and di- and triisopropylbenzene, and relatively smaller amounts of butylbenzene, propylene, oligomers, non-aromatics, etc. Propylene is essentially 100 percent reacted in the alkylation reaction zone, while benzene forms at least 50 molar percent and preferably 60 to 80 molar percent of the effluent. Accordingly, recirculation of a portion of the effluent to the inlet of the alkylation reaction zone increases the benzene/propylene ratio in the alkylation reaction zone.

Several benefits result as the benzene/propylene ratio increases in the alkylation reaction zone, including (1) a dilution of propylene molecules with benzene molecules favoring formation of isopropylbenzene (cumene) and limiting formation of propylene oligomers; and, (2) a benzene/propylene ratio greater than one is indicative of the presence of excess benzene, which acts as a heat sink to absorb heat generated by the exothermic alkylation reaction, and limit the formation of propylene oligomers and solid hydrocarbon deposits on the catalyst, both of which increase with higher temperature in the alkylation reaction zone. In prior art processes, a temperature increase from inlet to outlet of the alkylation reaction zone of about 20° to 40° C. is typical without quench, and in the present process, a similar temperature increase or lower is desired, and is attained by suitably increasing the flow rate of recirculated effluent.

The recirculated effluent stream may be indirectly cooled by cooling means such as a water cooled exchanger, an air cooled exchanger, or an exchanger in which another hydrocarbon stream is used as the coolant, to a temperature of about 150° to 260° C., i.e., to a temperature essentially equivalent to the temperature of the reaction zone inlet stream, or it may be admixed without cooling with a mixture of the propylene feed stream and the recycle benzene stream, the mixture being at a suitable temperature to provide an alkylation reaction zone inlet temperature of about 150° to 260° C., and preferably about 195° to 215° C. Furthermore, a third portion of the reaction zone effluent stream may be indirectly cooled by similar cooling means as stated hereinabove to a temperature of about 35° to 150° C. and passed into the reaction zone at suitable points to act as quench to cool the reactants and prevent excessive increase of temperature from inlet to outlet of the alkylation reaction zone. When the alkylation catalyst employed is a supported catalyst, for example solid phosphoric acid, suitable quench points may be chosen by dividing the catalyst bed into several successive separate beds and passing a portion of the quenching medium between each of the successive beds. In a preferred mode of operation, a portion of alkylation reaction zone effluent is cooled to about 35°–95° C. and introduced into the reaction mixture as a quenching medium between at least two successive catalyst beds in an amount sufficient to reduce the temperature of the reaction mixture to within about −4° C. of the temperature of the reaction mixture entering the last preceding catalyst bed.

As recirculation of alkylation reaction zone effluent to the inlet of the reaction zone increases, the concentration of cumene in the alkylation reaction zone also increases, thus providing more potential sites for polyalkylated benzene products and resulting in increased production of di- and triisopropylbenzene as compared to prior art processes. Whereas di- and triisopropylbenzene production in prior art processes is typically less than 5 mole percent as compared with cumene production, the present process results in 5 to 20 mole percent or more.

Propane, butane, benzene, and cumene comprises about 90 to 95 mole percent of the alkylation reaction zone effluent, and toluene, butylbenzene, di- and triisopropylbenzene, propylene oligomers and other components in trace amounts comprise 10 to 5 mole percent. The net alkylation zone effluent stream withdrawn from the alkylation reaction zone is passed separately or in admixture with a transalkylation reaction zone effluent stream set forth hereinbelow into a separation zone, wherein by means of a combination of fractional distillation, absorption, stripping, and flashing, the desired components are separated at separation conditions selected to minimize utility consumption. Product streams withdrawn from the separation zone include a propane-rich stream, a cumene stream, a butylbenzene-rich stream, a propylene oligomer stream, and a benzene drag stream, the lastly stated stream serving to remove trace quantities of non-aromatic components boiling between propane and cumene.

The present inventive concept is not limited by a specific combination of separation steps, however the separation of excess benzene and cumene is at present most economically accomplished by fractional distillation, in which benzene and lighter components are separated into an overhead fraction and cumene and heavier components are separated into a bottoms fraction. The separation of excess benzene in prior art processes has a relatively large capital and utility requirement resulting from the greater quantity of excess benzene separated from cumene as compared with the present process. While benzene/cumene molar ratios in the reaction zone net effluent of prior art processes is about 6.5, this ratio in the present process is about 2 to 5 at constant molar benzene/cumene ratio in the alkylation reaction zone. Excess benzene separated from the alkylation reaction zone effluent may be withdrawn from the process as a product stream, but preferably a first portion is passed to the inlet of the alkylation reaction zone as a recycle benzene-rich stream and a second portion is passed into a transalkylation reaction zone in admixture with a di- and triisopropylbenzene-rich stream, also separated and withdrawn from the separation zone. The admixture of benzene and di- and triisopropylbenzene is passed into a transalkylation reaction zone, wherein the reactants combine to produce cumene.

The inventive process of the present invention is not limited by the catalyst incorporated in the transalkylation reation zone. Various catalyts are known to one skilled in the art, such as a boron tri-fluoride-modified inorganic oxide catalyst described in U.S. Pat. No. 3,200,163, an acid extracted crystalline aluminosilicate catalyst described in U.S. Pat. No. 3,551,510, or a fluorine containing refractory inorganic oxide described in U.S. Pat. No. 3,205,277. Preferred as a transalkylation catalyst in the present invention is a solid phoshoric acid catalyst prepared in a similar manner as the one used hereinabove in the alkylation reaction zone, or especially preferred is a solid phosphoric acid catalyst containing 70 to 90 weight percent phosphorous. The transalkylation zone may be equipped with heat transfer means, baffles, trays, heating means, pumping means, etc. The reaction zone is preferably of the adibatic type, and is not limited by reactor design or configuration. Conditions utilized in the transalkylation reaction zone may be varied over a relatively wide range; the transalkylation reaction may be effected at temperatures of from 35° to 370° C., at pressures of about 15 to 200 atmospheres, at molar benzene/polyisopropylbenzene ratio of about 4 to 16, and liquid hourly space velocity based on reaction zone effluent of 0.1 to 20. With the preferred solid phosphoric acid catalyst, transalkylation reacton conditions include a temperature of about 175° to 290° C., a pressure of about 20 to 40 atmospheres, molar benzene/polypropylbenzene ratio of about 4 to 16, and liquid hourly space velocity based on reaction zone effluent of 0.5 to 5.0 As described hereinabove, effluent of the transalkylation reaction zone is passed into the separation zone.

I claim as my invention:
1. A process for the production of cumene which comprises the steps of:
 a. reacting propylene with an excess of benzene in the presence of an alkylation catalyst at alkylation reaction conditions in an alkylation reaction zone;
 b. dividing the total liquid effluent of said zone into at least two portions of like composition;

c. recirculating one of said portions of the effluent to said reaction zone;
d. introducing another of said portions of said effluent and a transalkylation zone effluent stream, formed as hereinafter set forth, into a separation zone;
e. separating from the admixed effluents in the separation zone a benzene-rich stream, a cumene product stream and a di- and triisopropylbenzene-rich stream;
f. transalkylating the last named stream with benzene in the presence of a transalkylation catalyst in a transalkylation zone to form additional cumene;
g. supplying the effluent of the last mentioned zone to said separation zone as said transalkylation zone effluent stream;
h. passing at least a portion of said benzene-rich stream from the separation zone to said alkylation reaction zone; and
i. recovering said cumene product stream from the separation zone.

2. The process of claim 1 further characterized in that at least a portion of the benzene for reaction with the propylene in step (a) is supplied to said separation zone.

3. The process of claim 1 further characterized in that at least a portion of the benzene reactant for step (f) is supplied to said separation zone and then to the transalkylation zone.

4. The process of claim 1 further characterized in that the benzene for reaction in steps (a) and (f) is supplied to said separation zone.

5. The process of claim 1 further characterized in that at least a portion of the benzene-rich stream from the separation zone is supplied to said transalkylation zone.

6. The process of claim 1 further characterized in that said alkylation catalyst is a solid phosphoric acid catalyst.

7. The method of claim 1 further characterized in that said transalkylation catalyst is a solid phosphoric acid catalyst.

8. The method of claim 1 further characterized in that said alkylation catalyst is a solid phosphoric acid catalyst containing from about 50 to about 75 wt. % phosphorus, and said transalkylation catalyst is a solid phosphoric acid containing from about 70 to about 90 wt. % phosphorus.

9. The method of claim 1 further characterized in that the molar ratio of benzene to propylene in said alkylation zone is from about 2:1 to about 6:1 without inclusion of said one portion of the alkylation zone effluent stream.

10. The process of claim 1 further characterized in that said phosphoric acid catalyst in said alkylation reaction zone is in the form of at least two successive catalyst beds and a third portion of said effluent from the alkylation zone is cooled to a temperature of from about 35° to about 150° C. and introduced into the reaction mixture between at least two successive catalyst beds as quenching medium.

11. The process of claim 1 further characterized in that said first portion of the effluent from the alkylation zone is cooled to a temperature of from about 150° to about 260° C.

* * * * *